United States Patent
Kobayashi et al.

(10) Patent No.: US 12,064,220 B2
(45) Date of Patent: Aug. 20, 2024

(54) VENOUS PRESSURE MEASUREMENT APPARATUS

(71) Applicant: NIHON KOHDEN CORPORATION, Tokyo (JP)

(72) Inventors: Naoki Kobayashi, Tokorozawa (JP); Haruka Morimoto, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 790 days.

(21) Appl. No.: 16/585,605

(22) Filed: Sep. 27, 2019

(65) Prior Publication Data

US 2020/0100689 A1  Apr. 2, 2020

(30) Foreign Application Priority Data

Sep. 28, 2018 (JP) .................. 2018-184192

(51) Int. Cl.
*A61B 5/021* (2006.01)
*A61B 5/022* (2006.01)
*A61B 5/0235* (2006.01)

(52) U.S. Cl.
CPC ...... *A61B 5/02141* (2013.01); *A61B 5/02116* (2013.01); *A61B 5/02225* (2013.01); *A61B 5/02133* (2013.01); *A61B 5/0235* (2013.01)

(58) Field of Classification Search
None
See application file for complete search history.

(56) References Cited

U.S. PATENT DOCUMENTS

| | | | |
|---|---|---|---|
| 5,671,750 A | * | 9/1997 | Shinoda ............... A61B 5/0285 600/490 |
| 2011/0144918 A1 | | 6/2011 | Inoue |
| 2012/0253209 A1 | | 10/2012 | Ukawa et al. |
| 2015/0245772 A1 | | 9/2015 | Kawamoto et al. |
| 2016/0213332 A1 | | 7/2016 | Ukawa et al. |

(Continued)

FOREIGN PATENT DOCUMENTS

| | | |
|---|---|---|
| EP | 2420186 A1 | 2/2012 |
| EP | 2912996 A1 | 9/2015 |
| JP | 2012-205822 A | 10/2012 |

(Continued)

OTHER PUBLICATIONS

Machine Translation of JP2017029622A. Retrieved from Espacenet on Jun. 8, 2022. (Year: 2022).*

(Continued)

*Primary Examiner* — Benjamin S Melhus
*Assistant Examiner* — Samuel C Kim
(74) *Attorney, Agent, or Firm* — Sughrue Mion, PLLC (57) ABSTRACT

A venous pressure measurement apparatus includes: a pressure controller that causes an internal pressure of a cuff to be attached to a subject, to change; a pressure detector that detects the internal pressure of the cuff; and a processor that causes the pressure controller to change the internal pressure of the cuff, acquires a statistical value relating to a distribution of amplitudes of a plurality of pressure changes corresponding to pressure vibration that occurs in the cuff, and that is detected by the pressure detector, and estimates a venous pressure of the subject based on a change of the statistical value due to the change of the internal pressure of the cuff.

7 Claims, 6 Drawing Sheets

(56) References Cited

U.S. PATENT DOCUMENTS

2018/0206744 A1    7/2018   Ukawa et al.

FOREIGN PATENT DOCUMENTS

| | | | |
|---|---|---|---|
| JP | 5694032 B2 | 4/2015 | |
| JP | 2015-160082 A | 9/2015 | |
| JP | 2016-137087 A | 8/2016 | |
| JP | 2017-29622 A | 2/2017 | |
| WO | WO-0224053 A2 * | 3/2002 | ............. A61B 5/022 |

OTHER PUBLICATIONS

Communication dated Nov. 4, 2019, from the European Patent Office in counterpart European Application No. 19200208.7.

* cited by examiner

VENOUS PRESSURE MEASUREMENT APPARATUS

CROSS-REFERENCE TO RELATED APPLICATIONS

This application is based upon and claims the benefit of priority from prior Japanese patent application No. 2018-184192, filed on Sep. 28, 2018, the entire contents of which are incorporated herein by reference.

TECHNICAL FIELD

The presently disclosed subject matter relates to an apparatus that measures the venous pressure by using a cuff which is attached to the subject.

BACKGROUND

Japanese Patent No. 5,694,032 discloses a venous pressure measurement apparatus of this kind. The apparatus estimates the mean venous pressure of a subject by using two cuffs that are attached to the upper arm of the subject. Specifically, the internal pressure of a first cuff that is produced when the correlation between a first pressure vibration that occurs in the first cuff by the artery pressure pulse wave and the venous pressure pulse wave, and a second pressure vibration that occurs in a second cuff by at least the artery pressure pulse wave is minimum is estimated as the mean venous pressure of the subject. The estimation is based on that the amplitude of the venous pressure pulse wave seems to be maximum when the pressure difference between the inside and outside of the venous blood vessel is minimized, and also that the correlation between the pressure vibrations caused in the cuffs seems to be smaller the lager the venous pressure pulse wave component.

A pulse wave signal corresponding to the second pressure vibration may be acquired also by another sensor that is different from the first cuff which is attached to the finger tip of the subject.

SUMMARY OF INVENTION

It is an object of the presently disclosed subject matter to provide an apparatus that can accurately estimate the venous pressure of the subject although using a single cuff.

According to an aspect of the presently disclosed subject matter, there is provided a venous pressure measurement apparatus including: a pressure controller that causes an internal pressure of a cuff to be attached to a subject, to change; a pressure detector that detects the internal pressure of the cuff; and a processor that causes the pressure controller to change the internal pressure of the cuff, acquires a statistical value relating to a distribution of amplitudes of a plurality of pressure changes corresponding to pressure vibration that occurs in the cuff, and that is detected by the pressure detector, and estimates a venous pressure of the subject based on a change of the statistical value due to the change of the internal pressure of the cuff.

According to an aspect of the presently disclosed subject matter, there is also provided a venous pressure measurement apparatus including: a pressure controller that causes an internal pressure of a cuff which is attached to a subject, to change; a pressure detector that detects the internal pressure of the cuff; and a processor that causes the pressure controller to change the internal pressure of the cuff, acquires an index value indicating a manner of a pressure change corresponding to pressure vibration that occurs in the cuff, and that is detected by the pressure detector, and estimates a venous pressure of the subject based on a change of the index value due to the change of the internal pressure of the cuff.

DESCRIPTION OF EMBODIMENTS

Figure 1:
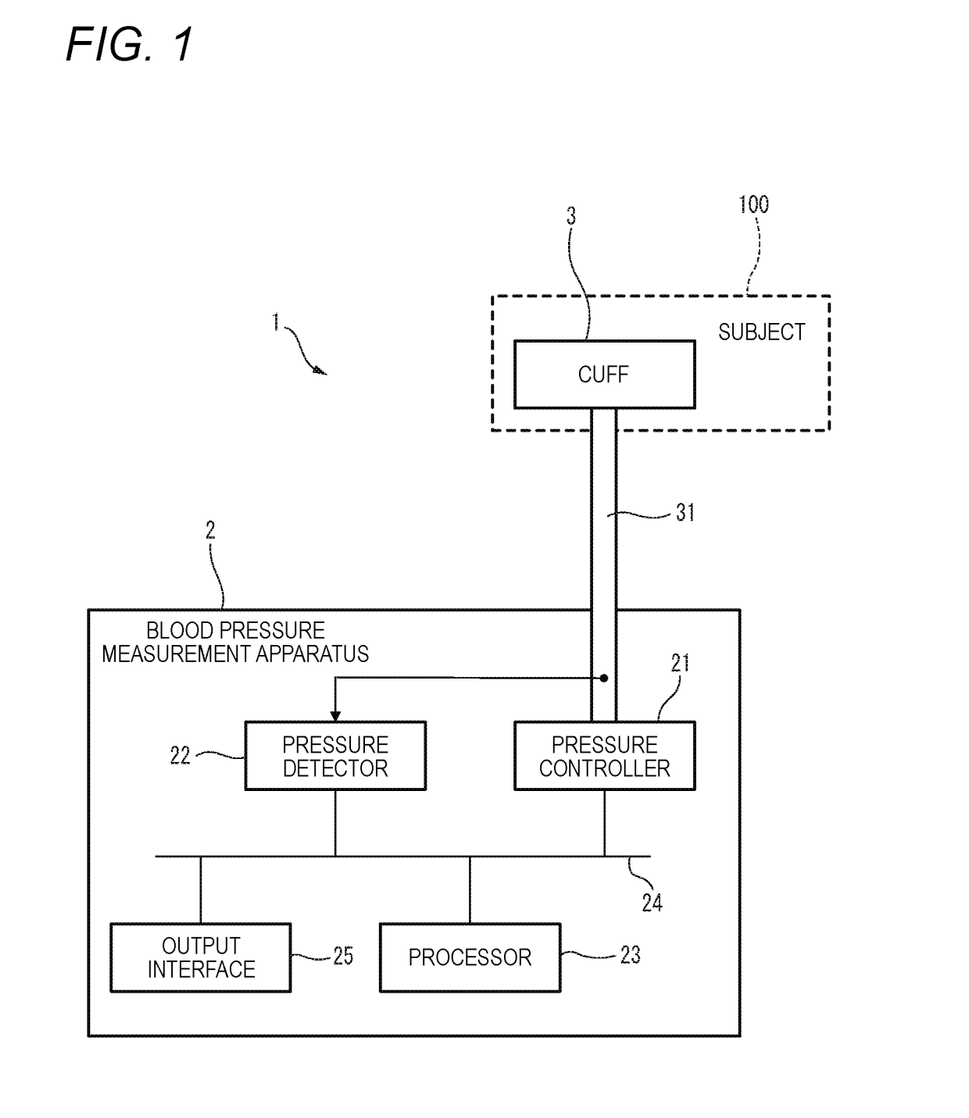
FIG. 1 illustrates the functional configuration of a blood pressure measurement system of an embodiment.

Hereinafter, an embodiment will be described in detail with reference to the accompanying drawings. FIG. 1 illustrates the functional configuration of a blood pressure measurement system 1 of an embodiment. The blood pressure measurement system 1 may include a blood pressure measurement apparatus 2 and a cuff 3.

The blood pressure measurement apparatus 2 is an apparatus that measures the blood pressure of a subject 100 by using the cuff 3 which is attached to the subject. The blood pressure measurement apparatus 2 is an example of the venous pressure measurement apparatus. That is, the blood pressure measurement apparatus 2 may measure only the venous pressure of the subject, or may measure the artery pressure in addition to the venous pressure.

The blood pressure measurement apparatus 2 may include a pressure controller 21, a pressure detector 22, a processor 23, and a communication bus 24.

The pressure controller 21 is connected to the cuff 3 through a tube 31. The pressure controller 21 may include a pump mechanism and a valve mechanism. The pump mechanism feeds the air into the cuff 3 through the tube 31 to raise the internal pressure of the cuff 3. The valve mechanism makes or breaks communication between the tube 31 and the ambient air. When the tube 31 and the ambient air are communicated with each other during non-operation of the pump mechanism, the internal pressure of the cuff 3 is lowered.

The pressure detector 22 detects the internal pressure of the cuff 3. The pressure detector 22 may include, for example, a pressure sensor that detects the internal pressure of the cuff 3 through the tube 31.

The processor 23 can communicate signals and date with the pressure controller 21 and the pressure detector 22 through the communication bus 24. Each of the pressure controller 21 and the pressure detector 22 may appropriately include an interface circuit such as an A/D converter in order to provide signals and date having forms that can be processed by the processor 23.

Figure 2:
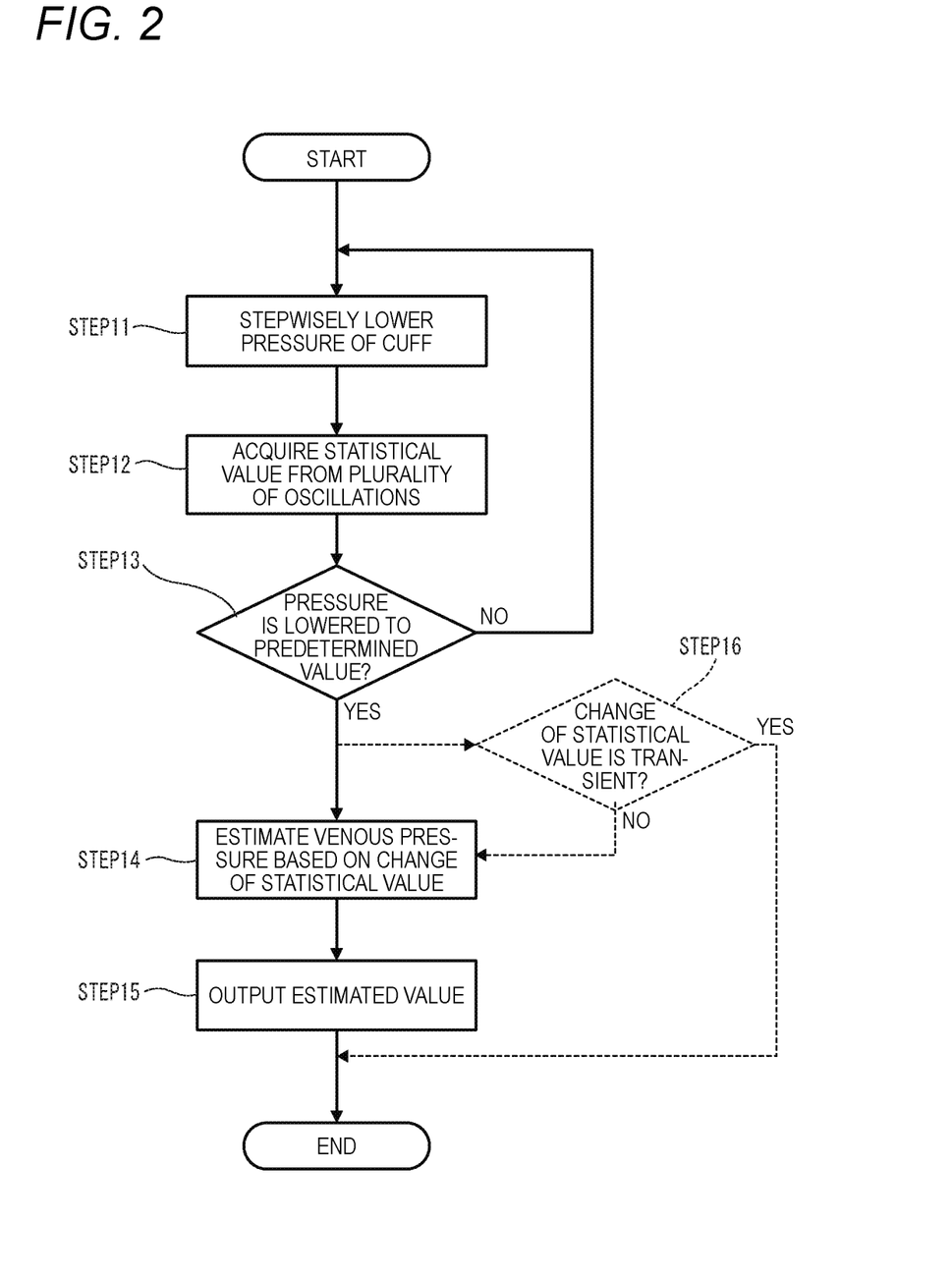
FIG. 2 illustrates an operation example of a blood pressure measurement apparatus in FIG. 1.

FIG. 2 illustrates an example of the flow of processes that are performed by the processor 23. The processor 23 causes the pressure controller 21 to stepwisely lower the internal pressure of the cuff 3 (STEP 11). That is, the pressure controller 21 performs a pressure control so that a state where the internal pressure of the cuff 3 has one of a plurality of setting values is continued for a predetermined time period, and, after the predetermined time period elapses, the internal pressure of the cuff 3 has one of a plurality of lower setting values.

Figure 3A:
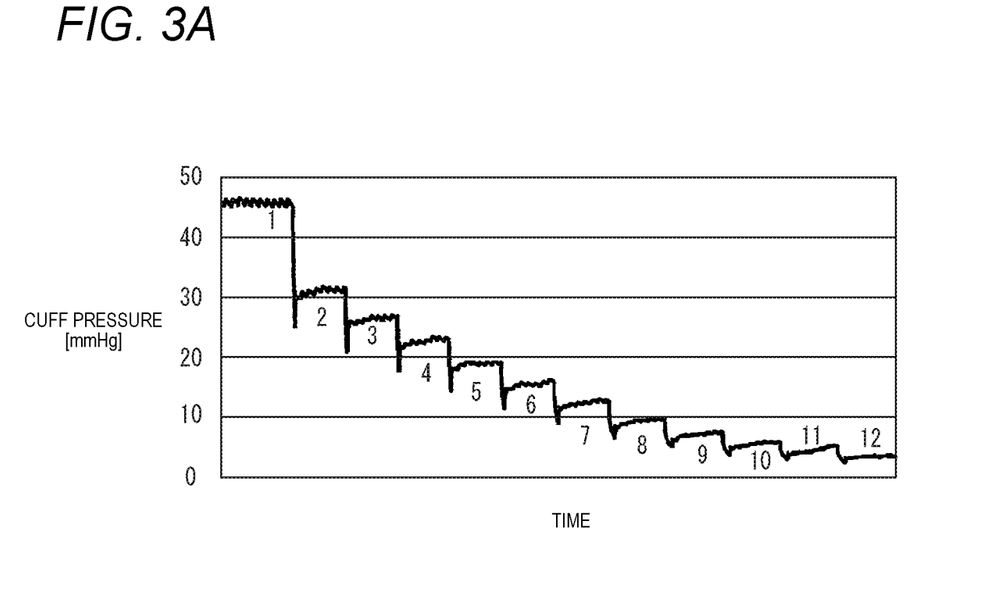
FIGS. 3A and 3B illustrate an estimation of the venous pressure based on the operation of FIG. 2.

FIG. 3A illustrates an example of a change over time of the internal pressure of the cuff 3 that is detected by the pressure detector 22. In the example, the pressure controller 21 performs a pressure control so that the internal pressure of the cuff 3 is stepwisely lowered among 12 setting values.

The waveform of FIG. 3A illustrating a change over time of the internal pressure of the cuff 3 contains vibration waveforms having frequency components that are higher as compared with the stepwise lowering of the internal pressure. The vibration waveforms reflect the pressure vibration (oscillation) that occurs in the cuff 3 in accordance with pulsations of the subject 100.

Figure 3B:
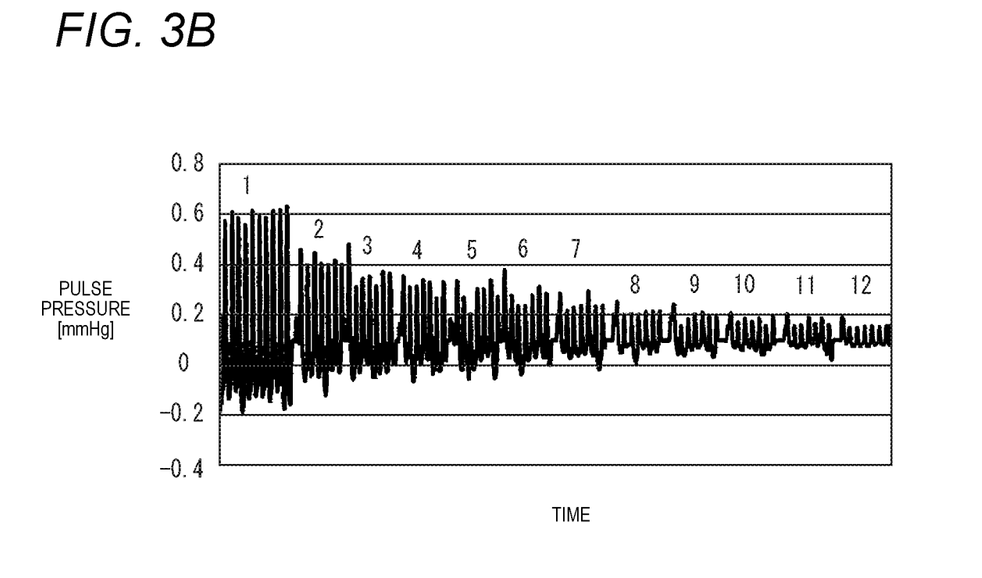

FIG. 3B illustrates a change over time of the oscillation component that is extracted from the waveform of FIG. 3A illustrating a change over time of the internal pressure of the cuff 3. The extraction of the oscillation component may be performed by applying a frequency filtering process to the waveform of FIG. 3A. The frequency filtering process may be performed by causing the waveform to be passed through a high-pass filter circuit that may be provided in the pressure detector 22, or in a software-like manner by the processor 23.

As illustrated in FIG. 3B, during a period when the state where the internal pressure of the cuff 3 has one of the plurality of setting values is continued, a plurality of oscillation waveforms are contained. In other words, the duration time period of a state where the internal pressure of the cuff 3 has one of the plurality of setting values is determined so as that a plurality of oscillation waveforms are contained within the time period.

Then, the processor 23 acquires a statistical value relating to the distribution of the amplitudes of a plurality of oscillation waveforms (STEP 12 of FIG. 2). In other words, the processor 23 acquires a statistical value relating to the distribution of the amplitudes of a plurality of pressure changes corresponding to pressure vibration that occurs in the cuff 3, and that is detected by the pressure detector 22, in a state where the internal pressure of the cuff 3 is set to one of the plurality of setting values.

Figure 4A:
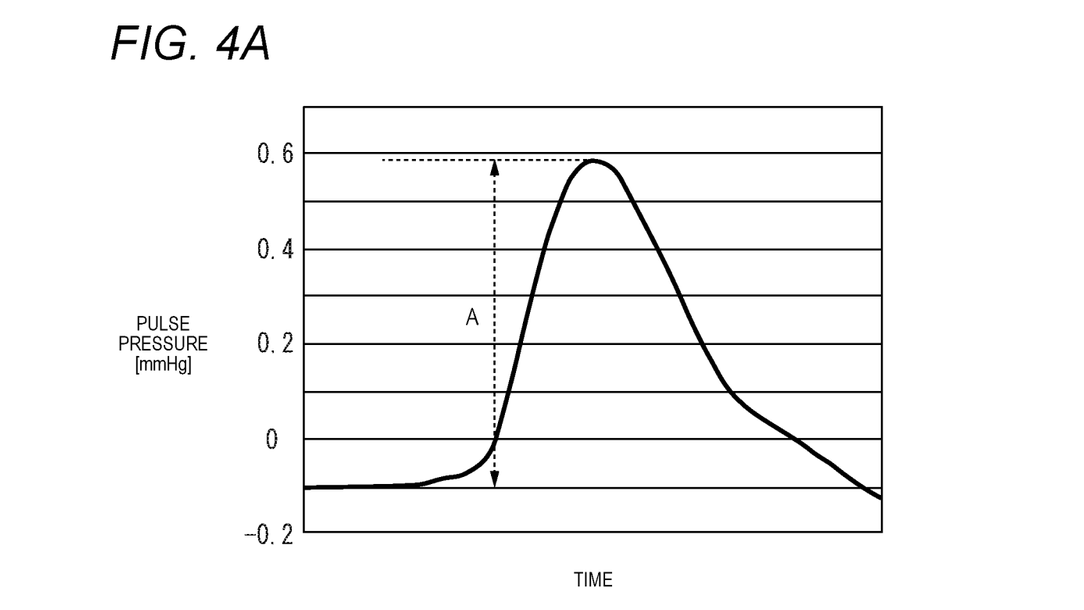
FIGS. 4A and 4B illustrate an estimation of the venous pressure based on the operation of FIG. 2.

FIG. 4A illustrates an example of the oscillation waveform extracted in the above-described process. The single oscillation waveform corresponds to pressure vibration that occurs in the cuff 3 in response to one pulsation. The amplitude A of the oscillation waveform may be defined, for example, as the difference between the minimum and maximum values of the pulse pressure in the rising portion of the waveform.

Examples of the statistical value are the mean, median, and mode values of amplitudes A of a plurality of oscillation waveforms. Alternatively, the sum of squares or root mean square (RMS) of a plurality of oscillation waveforms from which the DC component is eliminated may be used as the statistical value reflecting the amplitude A. The sum of squares, the RMS, or the like may be calculated for each of oscillation waveforms, and then the mean, median, mode values, or the like of the values may be identified for a plurality of oscillation waveforms. Statistical values of two or more types may be acquired.

When at least one statistical value is acquired, the processor 23 determines whether the internal pressure of the cuff 3 is lowered to a predetermined value or not (STEP 13 of FIG. 2). If the internal pressure of the cuff 3 is not lowered to the value indicated by the reference numeral 12 in FIG. 3A (N in STEP 13 of FIG. 2), the process returns to STEP 11. The internal pressure of the cuff 3 is lowered to the next setting value, and, during a period when the setting value is maintained, the at least one statistical value is acquired for a plurality of oscillation waveforms corresponding to pressure vibration that occurs in the cuff 3, and that is detected by the pressure detector 22.

The stepwise lowering of the internal pressure of the cuff 3 may be performed in parallel with the process of acquiring a statistical value. Although, in the above example, the internal pressure of the cuff 3 is stepwisely lowered every elapse of the predetermined time period, the apparatus may be configured so that, when a predetermined number of oscillation waveforms are acquired, the internal pressure of the cuff 3 is lowered by one step.

Figure 4B:
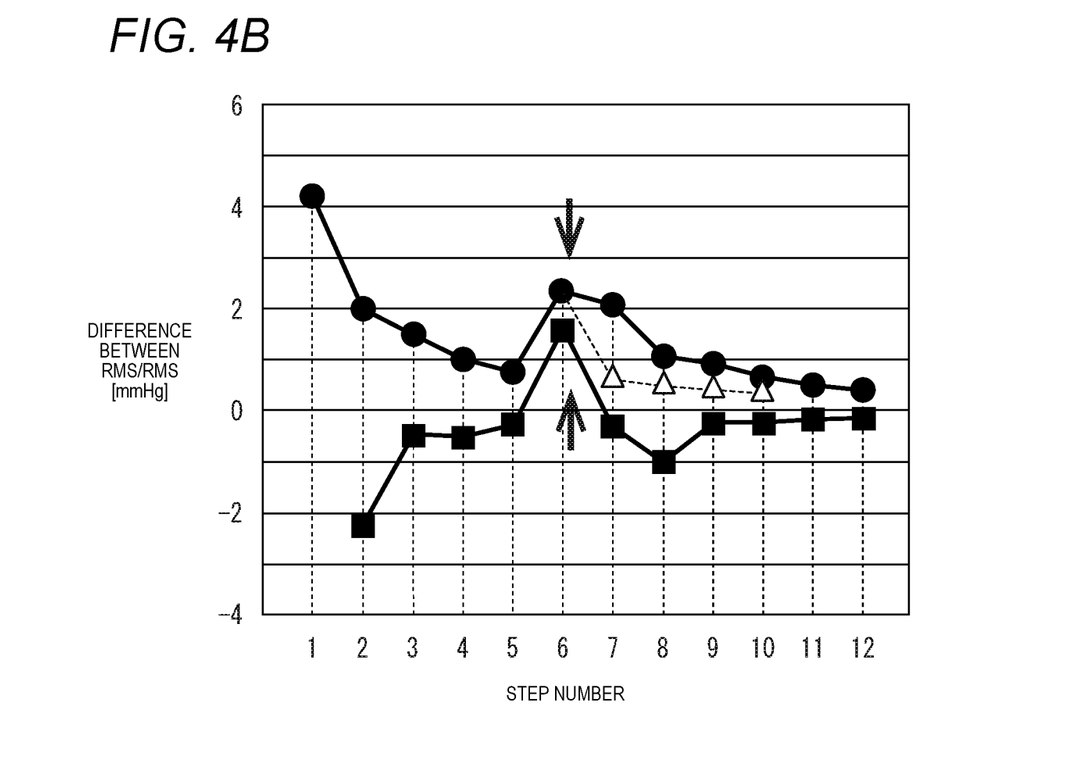

FIG. 4B illustrates a change of the acquired statistical value due to the stepwise lowering of the internal pressure of the cuff 3. The circular plots indicate the RMS of a plurality of oscillation waveforms corresponding to pressure vibration that occurs in the cuff 3, and that is detected by the pressure detector 22, in a state where the internal pressure of the cuff 3 is at one of the plurality of setting values. The step numbers of the abscissa correspond to the step numbers of the stepwise lowering that are attached to the waveforms illustrated in FIGS. 3A and 3B. Each of the square plots indicates the difference value between the RMS that is calculated in a certain step (one of the plurality of setting values), and the RMS that is calculated in the step which is previous to the pressure lowering in the certain step.

When the internal pressure of the cuff 3 is lowered to the value indicated by the reference numeral 12 in FIG. 3A (Y in STEP 13 of FIG. 2), the processor 23 estimates the venous pressure of the subject 100 based on a change of the acquired statistical value due to the stepwise lowering of the internal pressure of the cuff 3 (STEP 14 of FIG. 2).

The above-described oscillation waveforms are detected by the pressure detector 22 as a phenomenon in which the artery pressure pulse wave and venous pressure pulse wave of the subject 100 are superimposed on each other. It is known that, when the internal pressure of the cuff 3 is lower than the mean artery pressure, the amplitude of the artery pressure pulse wave is monotonously reduced with lowering of the internal pressure of the cuff 3. It is further known that the amplitude of the venous pressure pulse wave is maximum in the case where the internal pressure of the cuff 3 is equal to the mean venous pressure of the subject 100. The inventor of the present invention has conceived that the internal pressure value of the cuff 3 at which the amplitude of the oscillation waveform is maximum is identified within the pressure range that seems to include the mean venous pressure, thereby enabling the venous pressure of the subject 100 to be accurately estimated by using the single cuff 3.

In the example illustrated in FIG. 4B, the change of the RMS shows the maximal value in step number 6 of the stepwise pressure lowering, and that of the difference value between the RMSs shows the maximum value. These values appear in the change of the statistical value as the inflection point that reflects the state where the amplitude of the oscillation waveform is maximum. "Inflection point" as used herein is a local maximal or minimal point. In the example, the processor 23 estimates the setting value of the internal pressure of the cuff 3 corresponding to step number 6 of the stepwise pressure lowering, as the venous pressure of the subject 100.

According to the configuration, while using the single cuff 3 (without attaching an additional cuff or sensor to the subject 100), the venous pressure of the subject 100 can be accurately estimated. Moreover, the venous pressure of the subject 100 is estimated by using the statistical value relating to the distribution of the amplitudes of a plurality of oscillation waveforms, and therefore the influence of noises can be suppressed, and the accuracy of the estimation can be improved.

In the embodiment, the pressure controller 21 performs the control so that the internal pressure of the cuff 3 is stepwisely lowered. According to the configuration, a plurality of oscillation waveforms that are acquired under the same internal pressure condition are used in the statistical process, and therefore the increase of the computational load of the processor 23 can be suppressed.

Alternatively, the pressure controller 21 may perform the control so that the internal pressure of the cuff 3 is continuously lowered. In the alternative, a plurality of time ranges or pressure ranges are set so that a plurality of oscillation waveforms are acquired in each range, and the above-described statistical value is acquired in each of the ranges. Also in such a configuration, the venous pressure of the subject 100 may be estimated based on a change of the statistical value due to a change of the internal pressure of the cuff 3.

As illustrated in FIG. 2, the processor 23 may determine whether the change of the acquired statistical value is transient or not (STEP 16). It is determined whether the change is transient or not, based on the magnitude of the change of the statistical value before and after the appearance of the inflection point. If it is determined that the change of the statistical value is not transient (N in STEP 16), the processor 23 executes the above-described estimation of the venous pressure (STEP 14). If it is determined that the change of the statistical value is transient (Y in STEP 16), the processor 23 terminates the process or again preforms the measurement. Alternatively, the processor 23 eliminates the statistical value that is determined to be transient, and then executes the estimation of the venous pressure. This is performed because, in the case where the change of the statistical value is transient, there is a high possibility that this change may be caused by noises containing an arrhythmia. According to the configuration, therefore, reduction of the accuracy of the measurement of the venous pressure that is due to an influence of noises containing an arrhythmia can be suppressed.

In the case of the example illustrated in FIG. 4B, the maximal value of the RMS appears in step number 6. The maximal value is obtained by significant rising from the value of the RMS that is acquired in step number 5. In the case where the significant rising of the value is caused by noises and transient, the value of the RMS exhibits a significant lowering in step number 7 as indicated by the broken line and the triangular symbols in the figure. In the case where the value is smaller than the value of the RMS that is acquired in step number 5, or the lowering amount of the value is larger than a predetermined value, the processor 23 determines that the change of the RMS containing the appearance of the maximal value in step number 6 is transient.

By contrast, in the case where the change of the RMS is normal, the value of the RMS that is acquired in step number 7 is larger than the value of the RMS that is acquired in step number 5, or the lowering amount of the value is equal to or smaller than the predetermined value. In the case where such a change is confirmed at least one time after the appearance of the maximal Value, the processor 23 may determine that the change of the RMS containing the appearance of the maximal value in step number 6 is not transient.

The processor 23 may estimate a value that is smaller than the internal pressure of the cuff 3 at which the change of the statistical value indicates the inflection point, as the venous pressure of the subject 100. In the example illustrated in FIG. 4B, the internal pressure of the cuff 3 that corresponds to step number 7, and that is lowered by one step from the internal pressure of the cuff 3 corresponding to step number 6 in which the RMS exhibits the maximal value (or the difference value between the RMSs exhibits the maximum value) may be estimated as the venous pressure of the subject 100.

Since the artery pressure pulse wave that is superimposed on the oscillation waveform is monotonously reduced with the pressure lowering of the cuff 3, a value that is smaller than the value of the internal pressure of the cuff 3 corresponding to the inflection point of the change of the statistical value which indicates the state where the amplitude of the oscillation waveform is maximum may sometimes reflect the mean venous pressure of the subject 100. According to the above-described configuration, in such a case, the venous pressure of the subject 100 can be accurately estimated.

In the case where the change of the statistical value is smaller than the internal pressure of the cuff 3 indicating the inflection point, the internal pressure of the cuff 3 corresponding to a step number that is reduced by two or more steps may be employed as an estimated value, or a value that is obtained by uniformly reducing a predetermined value from the internal pressure of the cuff 3 at which the change of the statistical value indicates the inflection point may be employed as an estimated value.

As illustrated in FIG. 1, the blood pressure measurement apparatus 2 may further include an output interface 25. The output interface 25 can communicate signals and date with the processor 23 through the communication bus 24. The processor 23 causes the output interface 25 to output the estimated value of the venous pressure of the subject 100 as a measurement value (STEP 15 of FIG. 2).

The output interface 25 may include at least one of: a display device that visually outputs the measurement value; a sound output device that audibly outputs the measurement value; and a port that outputs the measurement value to an external device as data.

Figure 5:
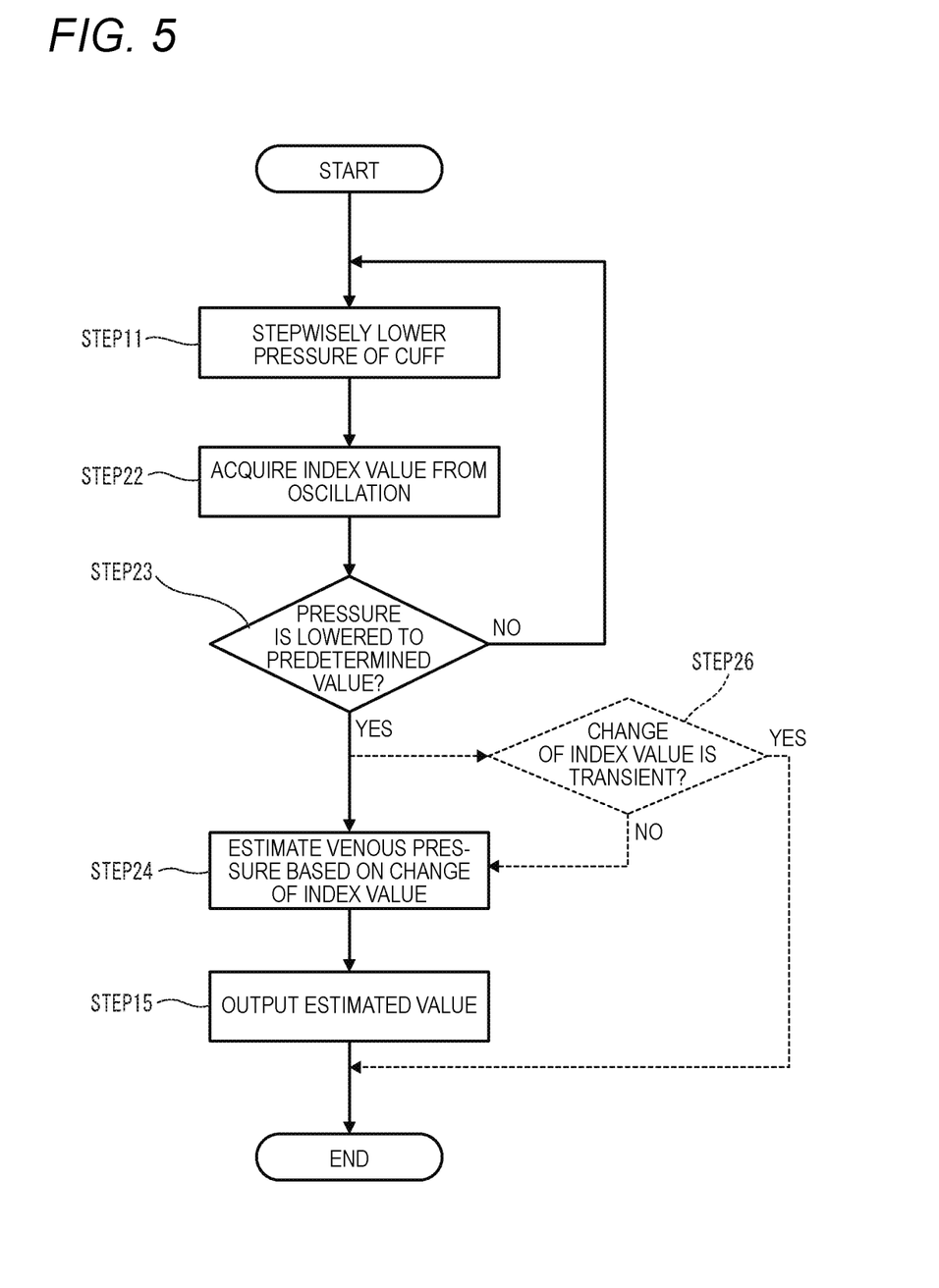
FIG. 5 illustrates another operation example of the blood pressure measurement apparatus in FIG. 1.

FIG. 5 illustrates another example of the flow of processes that are performed by the processor 23. The processes that are substantially identical with those illustrated in FIG. 2 are denoted by the same reference numerals, and the duplicated descriptions are omitted.

In the example, the processor 23 acquires an index value that indicates the manner of the pressure change, for at least one oscillation waveform (STEP 22). The duration time period of a state where the internal pressure of the cuff 3 is at one of the plurality of setting values is determined so that at least one oscillation waveform is contained within the time period. Examples of the index value that indicates the manner of the pressure change (i.e., the shape of the oscillation waveform) are the maximum pressure value, the minimum pressure value, the mean pressure value, the amplitude, the sum of squares, the RMS, the dispersion, the gradient, the peakedness, the distortion, the percentile, and the like. The oscillation waveform is indicated as a change over time of a plurality of pressure values that are acquired at a predetermined sampling rate. These index values are acquired by using at least one of the plurality of acquired pressure values. The acquired index values may have two or more types. The index value may be the mean, median, or mode value of a plurality of index values acquired for a plurality of oscillation waveforms.

Figure 6:
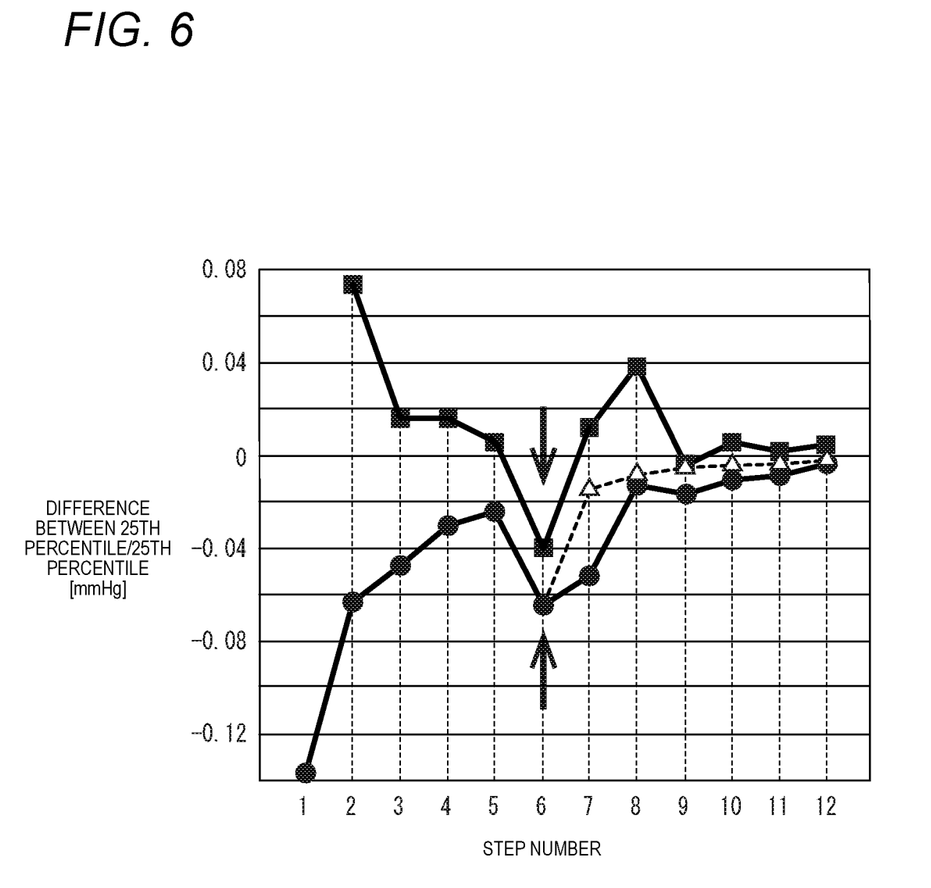
FIG. 6 illustrates an estimation of the venous pressure based on the operation of FIG. 5.

When the index value is acquired, the processor 23 determines whether the internal pressure of the cuff 3 is lowered to a predetermined value or not (STEP 23 of FIG. 5). If the internal pressure of the cuff 3 is not lowered to a value that is indicated by the reference numeral 12 illustrated in FIG. 3A (N in STEP 23 of FIG. 5), the process returns to STEP 11. The internal pressure of the cuff 3 is lowered to the next selling value, and, during a period when the setting value is maintained, the index value is acquired for at least one oscillation waveform corresponding to the pressure vibration that is detected by the pressure detector 22, and that occurs in the cuff 3. FIG. 6 illustrates the 25th percentile change of the oscillation waveform due to the stepwise lowering of the internal pressure of the cuff 3.

If the internal pressure of the cuff 3 is lowered to the value indicated by the reference numeral 12 in FIG. 3A (Y in STEP 23 of FIG. 5), the processor 23 estimates the venous pressure of the subject 100 based on a change of the acquired index value due to the stepwise lowering of the internal pressure of the cuff 3 (STEP 24 of FIG. 5).

The above-described oscillation waveforms are detected by the pressure detector 22 as a phenomenon in which the artery pressure pulse wave and venous pressure pulse wave of the subject 100 are superimposed on each other. It is known that, when the internal pressure of the cuff 3 is lower than the mean artery pressure, the amplitude of the artery pressure pulse wave is monotonously reduced with lowering of the internal pressure of the cuff 3. It is further known that the amplitude of the venous pressure pulse wave is maximum in the case where the internal pressure of the cuff 3 is equal to the mean venous pressure of the subject 100. It is still further known that the artery pressure pulse wave and the venous pressure pulse wave are different in phase and shape from each other. The inventor of the present invention has conceived that, when the internal pressure of the cuff 3 coincides with the mean venous pressure, the shape of the oscillation waveform exhibits a significant change. The inventor of the present invention has conceived that, when the value of the internal pressure of the cuff 3 at which a change of an index value that indicates the shape of the oscillation waveform is identified within the pressure range that seems to include the mean venous pressure, the venous pressure of the subject 100 can be accurately estimated by using the single cuff 3.

In an example illustrated in FIG. 6, in step number 6 of the stepwise pressure lowering, the 25th percentile change shows a significant minimal value. The value appears in the change of the index value as the inflection point that reflects the state where the shape change of the oscillation waveform is significant. In the example, the processor 23 estimates the setting value of the internal pressure of the cuff 3 corresponding to step number 6 of the stepwise pressure lowering, as the venous pressure of the subject 100.

The combination of the index value and the inflection point can be appropriately determined. In the case where the 75th percentile of the oscillation waveform is used as the index value, for example, the maximal value attracts attention as the inflection point that reflects the state where the shape change of the oscillation waveform is significant. In this case, the processor 23 estimates the setting value of the internal pressure of the cuff 3 at which the 75th percentile change exhibits the maximal value, as the venous pressure of the subject 100.

Also according to the configuration, although using the single cuff 3 (without attaching an additional cuff or sensor to the subject 100), the venous pressure of the subject 100 can be accurately estimated. Moreover, the venous pressure can be estimated based on at least one pressure vibration that occurs in the cuff 3, and therefore the measurement can be made faster.

The stepwise lowering of the internal pressure of the cuff 3 may be performed in parallel with the process of acquiring a statistical value. Alternatively, the pressure controller 21 may perform the control so that the internal pressure of the cuff 3 is continuously lowered. In the alternative, during a period when the internal pressure of the cuff 3 is continuously lowered to the predetermined value, a plurality of oscillation waveforms are detected, and the above-described index value is acquired for each of the oscillation waveforms. Also according to the configuration, the venous pressure of the subject 100 may be estimated based on a change of the index value due to a change of the internal pressure of the cuff 3.

As illustrated in FIG. 5, the processor 23 may determine whether the change of the acquired index value is transient or not (STEP 26). It is determined whether the change is transient or not, based on the magnitude of the change of the index value before and after the appearance of the inflection point. If it is determined that the change of the index value is not transient (N in STEP 26), the processor 23 executes the above-described estimation of the venous pressure (STEP 24). If it is determined that the change of the index value is transient (Y in STEP 26), the processor 23 terminates the process or again preforms the measurement. Alternatively, the processor 23 eliminates the index value that is determined to be transient, and then executes the estimation of the venous pressure. This is performed because, in the case where the change of the index value is transient, there is a high possibility that this change may be caused by noises containing an arrhythmia. According to the configuration, therefore, reduction of the accuracy of the measurement of the venous pressure that is due to an influence of noises containing an arrhythmia can be suppressed.

In the case of the example illustrated in FIG. 6, the 25th percentile minimal value appears in step number 6. The minimal value is obtained by significant lowering from the 25th percentile value that is acquired in step number 5. In the case where the significant lowering of the value is caused by noises and transient, the 25th percentile value exhibits a significant rising in step number 7 as indicated by the broken line and the triangular symbols in the figure. When the rising value is larger than a predetermined value, the processor 23 determines that the 25th percentile change containing the appearance of the minimal value in step number 6 is transient.

By contrast, in the case where the 25th percentile change is normal, the rising amount of the 25th percentile value that is acquired in step number 7, from the minimal value is equal to or smaller than the predetermined value. In the case where such a change is confirmed at least one time after the appearance of the minimal value, the processor 23 may determine that the 25th percentile change containing the appearance of the minimal value in step number 6 is not transient.

The processor 23 may estimate a value that is smaller than the internal pressure of the cuff 3 at which the change of the index value indicates the inflection point, as the venous pressure of the subject 100. In the example illustrated in FIG. 6, the internal pressure of the cuff 3 that corresponds to step number 7, and that is lowered by one step from the internal pressure of the cuff 3 corresponding to step number 6 in which the 25th percentile exhibits the significant minimal value may be estimated as the venous pressure of the subject 100.

Since the artery pressure pulse wave that is superimposed on the oscillation waveform is monotonously reduced with the pressure lowering of the cuff 3, a value that is smaller than the value of the internal pressure of the cuff 3 corresponding to the inflection point of the change of the index value which indicates the state where the amplitude of the oscillation waveform is maximum may sometimes reflect the mean venous pressure of the subject 100. According to the above-described configuration, in such a case, the venous pressure of the subject 100 can be accurately estimated.

In the case where the change of the index value is smaller than the internal pressure of the cuff 3 indicating the inflection point, the internal pressure of the cuff 3 corresponding to a step number that is reduced by two or more steps may be employed as an estimated value, or a value that is obtained by uniformly reducing a predetermined value from the internal pressure of the cuff 3 at which the change of the index value indicates the inflection point may be employed as an estimated value.

The above-described function of the processor 23 may be realized by a general-purpose microprocessor which operates in cooperation with a general-purpose memory. Examples of such a general-purpose microprocessor are a CPU, an MPU, and a GPU. Examples of such a general-purpose memory are a RAM and a ROM. A ROM may store programs that execute the above-described processes. The programs may include an artificial intelligence program. An example of an artificial intelligence program is a learned neural network with deep learning. The general-purpose microprocessor may designate at least part of the programs stored in the ROM, load the designated programs into the RAM, and execute the above-described processes in cooperation with the RAM.

The above-described function of the processor 23 may be realized by a dedicated integrated circuit such as a microcontroller, an FPGA, or an ASIC. At least part of the function of the processor 23 may be realized by a calculating device of a computer to which the blood pressure measurement apparatus 2 is connected.

The above-described embodiment is a mere example for facilitating understanding of the presently disclosed subject matter. The configuration of the embodiment may be adequately changed or improved without departing from the spirit of the presently disclosed subject matter.

In the above-described embodiment, the processor 23 estimates the venous pressure of the subject 100 while causing the pressure controller 21 to lower the internal pressure of the cuff 3. In this case, the embodiment may be easily integrated with a depressurization artery pressure measurement apparatus that is more prevalent. After the artery pressure is measured while the internal pressure of the cuff 3 is lowered in a higher numerical range, the measurement of the venous pressure can be efficiently performed. However, the processor 23 may estimate the venous pressure of the subject 100 while causing the pressure controller 21 to raise the internal pressure of the cuff 3. Namely, the processor 23 may cause the pressure controller 21 to stepwisely change (lower or raise) the internal pressure of the cuff 3 or to continuously change (lower or raise) the internal pressure of the cuff 3.

In the embodiment, the processor 23 may employ a value that is lower than the internal pressure of the cuff 3 at which a change of the statistical value or index value that is acquired indicates the inflection point, as an estimated value of the venous pressure. As far as the venous pressure is estimated based on the statistical value or index value that is acquired, however, a value at which these values indicate the inflection point, or a value that is higher than the internal pressure of the cuff 3 at which the value indicates the inflection point may be employed as an estimated value of the venous pressure.

According to an aspect of the presently disclosed subject matter, there is provided a venous pressure measurement apparatus including: a pressure controller that causes an internal pressure of a cuff to be attached to a subject, to change; a pressure detector that detects the internal pressure of the cuff; and a processor that causes the pressure controller to change the internal pressure of the cuff, acquires a statistical value relating to a distribution of amplitudes of a plurality of pressure changes corresponding to pressure vibration that occurs in the cuff, and that is detected by the pressure detector, and estimates a venous pressure of the subject based on a change of the statistical value due to the change of the internal pressure of the cuff.

The pressure vibration that occurs in the cuff is detected by the pressure detector as a phenomenon in which the artery pressure pulse wave and venous pressure pulse wave of the subject are superimposed on each other. It is known that, when the internal pressure of the cuff is lower than the mean artery pressure, the amplitude of the artery pressure pulse wave is monotonously reduced with lowering of the internal pressure of the cuff. It is further known that the amplitude of the venous pressure pulse wave is maximum in the case where the internal pressure of the cuff is equal to the mean venous pressure of the subject. The inventor of the present invention has conceived that the internal pressure value of a cuff at which the amplitude of the pressure vibration is maximum is identified within a pressure range that seems to include the mean venous pressure, thereby enabling the venous pressure of the subject to be accurately estimated by using the single cuff.

In association with a change of the internal pressure of the cuff among a plurality of setting values, for example, the maximal value may appear in change of the value of the root mean square of a plurality of pressure vibrations. The value reflects the state where the amplitude of the pressure vibration is maximum. In this case, the processor estimates the internal pressure of the cuff when the maximal value appears, as the venous pressure of the subject.

According to the configuration, while using the single cuff (without attaching an additional cuff or sensor to the subject), the venous pressure of the subject can be accurately estimated. Moreover, the venous pressure of the subject is estimated by using the statistical value relating to the distribution of the amplitudes of a plurality of pressure vibrations, and therefore the influence of noises can be suppressed, and the accuracy of the estimation can be improved.

According to an aspect of the presently disclosed subject matter, there is also provided a venous pressure measurement apparatus including: a pressure controller that causes an internal pressure of a cuff which is attached to a subject, to change; a pressure detector that detects the internal pressure of the cuff; and a processor that causes the pressure controller to change the internal pressure of the cuff, acquires an index value indicating a manner of a pressure change corresponding to pressure vibration that occurs in the cuff, and that is detected by the pressure detector, and estimates a venous pressure of the subject based on a change of the index value due to the change of the internal pressure of the cuff.

The pressure vibration that occurs in the cuff is detected by the pressure detector as a phenomenon in which the artery pressure pulse wave and venous pressure pulse wave of the subject are superimposed on each other. It is known that the amplitude of the artery pressure pulse wave when the internal pressure of the cuff is lower than the mean artery pressure is monotonously reduced with lowering the internal pressure of the cuff. It is known that the amplitude of the venous pressure pulse wave is maximum in the case where the internal pressure of the cuff is equal to the mean venous pressure. It is further known that the artery pressure pulse wave and the venous pressure pulse wave are different in phase and shape from each other. The inventor of the present invention has conceived that, when the internal pressure of the cuff coincides with the mean venous pressure, the shape of a waveform corresponding to the pressure vibration exhibits a significant change. The inventor of the present invention has conceived that, when the value of the internal pressure of the cuff at which a change of the index value that indicates the shape of a waveform corresponding to the pressure vibration is identified within the pressure range that seems to include the mean venous pressure, the venous pressure of the subject can be accurately estimated by using the single cuff.

In association with a change of the internal pressure of the cuff among a plurality of setting values, for example, the 25th percentile change can show a significant minimal value. The value reflects the state where a shape change of a waveform corresponding to a pressure vibration is significant. In this case, the processor estimates the internal pressure of the cuff when the minimal value appears, as the venous pressure of the subject.

Also according to the configuration, although using the single cuff (without attaching an additional cuff or sensor to the subject), the venous pressure of the subject can be accurately estimated. Moreover, the venous pressure can be estimated based on at least one pressure vibration that occurs in the cuff, and therefore the measurement can be made faster.

What is claimed is:

1. A venous pressure measurement apparatus comprising:
a cuff to be attached to a subject;
a pressure controller that causes an internal pressure of the cuff to lower or raise;
a pressure detector that detects the internal pressure of the cuff, the internal pressure of the cuff including oscillation components; and
a processor configured such that the processor:
causes the pressure controller to lower or raise the internal pressure of the cuff,
extracts the oscillation components by applying a frequency filter;
acquires a plurality of measures of a statistical value relating to the extracted oscillation components, and
estimates one venous pressure of the subject based on an inflection point of changes of the measures of the statistical value due to the lowering or raising of the internal pressure of the cuff;
if the pressure controller is caused to raise the internal pressure of the cuff, the processor is configured such that the processor estimates the one venous pressure as a value smaller than the internal pressure of the cuff when the changes of the measures of the statistical value indicates the inflection point, and
if the pressure controller is caused to lower the internal pressure of the cuff, the processor is configured such that the processor estimates the one venous pressure as a value greater than the internal pressure of the cuff when the changes of the measures of the statistical value indicates the inflection point;
wherein
the processor is configured such that the processor:
determines whether the inflection point of the changes of the measures of the statistical value is transient or not, and
the one venous pressure of the subject is estimated only if it is determined that the inflection point of the changes of the measures of the statistical value is not transient.

2. The venous pressure measurement apparatus according to claim 1, wherein
the processor is configured such that the processor:
causes the pressure controller to stepwisely or continuously lower or raise the internal pressure of the cuff among a plurality of setting values, and
acquires the measures of the statistical value during a period when the internal pressure of the cuff is at one of the plurality of setting values.

3. The venous pressure measurement apparatus according to claim 1, wherein
the pressure controller causes the internal pressure of the cuff to lower, and
the processor is configured such that the processor estimates the one venous pressure while causing the pressure controller to lower the internal pressure of the cuff.

4. A venous pressure measurement apparatus comprising:
a cuff to be attached to a subject;
a pressure controller that causes an internal pressure of the cuff to raise or lower;
a pressure detector that detects the internal pressure of the cuff, the internal pressure of the cuff including oscillation components; and
a processor configured such that the processor:
causes the pressure controller to raise or lower the internal pressure of the cuff,
extracts the oscillation components by applying a frequency filter;
acquires a plurality of measures of an index value components that are extracted from the internal pressure detected by the pressure detector indicating a parameter associated with the extracted oscillation components, and
estimates one venous pressure of the subject based on an inflection point of changes of the measures of the index value due to the lowering or raising of the internal pressure of the cuff;
if the pressure controller is caused to raise the internal pressure of the cuff, the processor is configured such that the processor estimates the one venous pressure as a value smaller than the internal pressure of the cuff when the changes of the measures of the index value indicates the inflection point, and
if the pressure controller is caused to lower the internal pressure of the cuff, the processor is configured such that the processor estimates the one venous pressure as a value greater than the internal pressure of the cuff when the changes of the measures of the index value indicates the inflection point;
wherein
the processor is configured such that the processor:

determines whether the inflection point of the changes of the measures of the index value is transient or not, and, the one venous pressure of the subject is estimated only if it is determined that the inflection point of the changes of the measures of the index value is not transient.

5. The venous pressure measurement apparatus according to claim 4, wherein the pressure controller causes the internal pressure of the cuff to lower, and the processor is configured such that the processor estimates the one venous pressure while causing the pressure controller to lower the internal pressure of the cuff.

6. A venous pressure measurement apparatus comprising:
a cuff to be attached to a subject;
a pressure controller that causes an internal pressure of the cuff to lower or raise;
a pressure detector that detects the internal pressure of the cuff, and
a processor configured such that the processor:
 causes the pressure controller to lower or raise the internal pressure of the cuff,
 acquires a plurality of measures of a statistical value relating to a shape change of a pulse waveform or a distribution of amplitudes of a plurality of pressure changes corresponding to pressure vibrations that occur in the cuff, and that are detected by the pressure detector,
 determines whether a change of the plurality of measures of the statistical value is transient or not, based on a magnitude of the changes of the plurality of measures of the statistical value before and after an inflection point of changes of the plurality of measures of the statistical value, and
 in response to a determination that the change of the plurality of measures of the statistical value is not transient, estimates one venous pressure of the subject based on the inflection point of the changes of the plurality of measures of the statistical value due to the lowering or raising of the internal pressure of the cuff.

7. A venous pressure measurement apparatus comprising:
a cuff to be attached to a subject;
a pressure controller that causes an internal pressure of the cuff to lower or raise;
a pressure detector that detects the internal pressure of the cuff; and
a processor configured such that the processor:
 causes the pressure controller to lower or raise the internal pressure of the cuff,
 acquires a plurality of measures of an index value indicating a shape change of a pulse waveform or a pressure change corresponding to pressure vibrations that occur in the cuff, and that are detected by the pressure detector,
 determines whether a change of the plurality of measures of the index value is transient or not, based on a magnitude of the changes of the plurality of measures of the index value before and after an inflection point of changes of the plurality of measures of the statistical value, and
 in response to a determination that the change of the plurality of measures of the index value is not transient, estimates one venous pressure of the subject based on the inflection point of the changes of the plurality of measures of the index value due to the lowering or raising of the internal pressure of the cuff.

* * * * *